United States Patent
Spangenberg et al.

(10) Patent No.: US 11,491,162 B2
(45) Date of Patent: Nov. 8, 2022

(54) COMBINATION OF QUINOLINE-4-CARBOXAMIDES AND BENZONAPHTHYRIDINE DERIVATIVES AS ANTIMALARIAL DRUG COMBINATION

(71) Applicant: Merck Patent GmbH, Darmstadt (DE)

(72) Inventors: Thomas Spangenberg, Geneva (CH); Claude Oeuvray, Duillier (CH); Nada Abla, Carouge (CH)

(73) Assignee: Merck Patent GmbH, Darmstadt (DE)

( * ) Notice: Subject to any disclaimer, the term of this patent is extended or adjusted under 35 U.S.C. 154(b) by 58 days.

(21) Appl. No.: 15/733,732

(22) PCT Filed: Apr. 9, 2019

(86) PCT No.: PCT/EP2019/058881
§ 371 (c)(1),
(2) Date: Oct. 7, 2020

(87) PCT Pub. No.: WO2019/197367
PCT Pub. Date: Oct. 17, 2019

(65) Prior Publication Data
US 2021/0023087 A1 Jan. 28, 2021

(30) Foreign Application Priority Data
Apr. 11, 2018 (EP) .................................... 18166769

(51) Int. Cl.
*A61K 31/5377* (2006.01)
*A61P 33/06* (2006.01)
*A61K 31/357* (2006.01)
*A61K 31/4745* (2006.01)

(52) U.S. Cl.
CPC ........ *A61K 31/5377* (2013.01); *A61K 31/357* (2013.01); *A61K 31/4745* (2013.01); *A61P 33/06* (2018.01)

(58) Field of Classification Search
CPC .............. A61K 31/5377; A61K 31/357; A61K 31/4745; A61P 33/06
See application file for complete search history.

(56) References Cited

FOREIGN PATENT DOCUMENTS

WO 2013/153357 10/2013

OTHER PUBLICATIONS

Derchering et al. "Modelling mosquito infection at natural parasite densities identifies drugs targeting EF2, PI4K or ATP4 as key candidates for interrupting malaria transmission" (2017) pp. 1-9 (Year: 2017).*

Croft et al., Review of pyronaridine anti-malarial properties and product characteristics, Aug. 2012, Malaria Journal, 270 (Year: 2012).*
Najahi et al, Synthesis and biological evaluation of new bis-indolone-N-oxides, Bioorganic Chemistry, vol. 48, 2013, pp. 16-21 (Year: 2013).*
Jittamala et al. "Pharmacokinetic Interactions between Primaquine and Pyroaridine-Artesunate in Healthy Adult Thai Subjects" (2015) pp. 505-513 (Year: 2015).*
Morrow GT. Designing a drug kit. Dent Clin North Am. Jan. 1982;26(1):21-33. PMID: 6948718. (Year: 1982).*
Han, H. "Targeted Prodrug Design to Optimize Drug Delivery." AAPS Pharmsci. (2000), vol. 2 (1) article 6, pp. 1-11. (Year: 2000).*
Ettmayer, P., et al. "Lessons Learned from Marketed and Investigational Prodrugs." J. Med. Chem. (2004) 47(10), pp. 2393-2404. (Year: 2004).*
Testa, B. "Prodrug research: futile or fertile?" Biochem. Pharm. (2004) 68, pp. 2097-2106. (Year: 2004).*
Berge, Stephen M., et al. "Pharmaceutical Salts." J. Pharmaceutical Sciences. (Jan. 1977) vol. 66, No. 1, pp. 1-19. (Year: 1977).*
Varma, Karthik. "Excipients used in the Formulation of Tablets." RRJCHEM (Jun. 2016), vol. 5, Issue 2, pp. 143-154. (Year: 2016).*
International Search Report dated Jul. 10, 2019 in PCT/EP2019/058881.
Written Opinion dated Jul. 10, 2019 in PCT/EP2019/058881.
Ayyoub et al., "Population Pharmacokinetics of Pyronaridine in Pediatric Malaria Patients," Antimicrobial Agents and Chemotherapy, Mar. 2016, vol. 60, No. 3, pp. 1450-1458.
Baragaña et al., "A novel multiple-stage antimalarial agent that inhibits protein synthesis," Nature 522, 315-320 (2015), 17 pages.
Piedade et al, "The pharmacogenetics of antimalaria artemisinin combination therapy," Expert Opin. Drug Metab. Toxicol. (2011) 7(10): 1185-1200.
Rottmann, et al., "Preclinical Antimalarial Combination Study of M5717, a Plasmodium falciparum Elongation Factor 2 Inhibitor, and Pyronaridine, a Hemozoin Formation Inhibitor," Antimicrobial Agents and Chemotherapy, Apr. 2020, vol. 64, Issue 4, 9 pages.

* cited by examiner

*Primary Examiner* — John S Kenyon
*Assistant Examiner* — Gillian A Hutter
(74) *Attorney, Agent, or Firm* — Grüneberg and Myers PLLC

(57) ABSTRACT

A combination includes as a first active ingredient 6-fluoro-2-(4-morpholin-4-ylmethyl-phenyl)-quinoline-4-carboxylic acid (2-pyrrolidin-1-yl-ethyl)-amide or a prodrug or pharmaceutically acceptable salt thereof and as a second active ingredient pyronaridine or a prodrug or pharmaceutically acceptable salt thereof. Also, a combination includes three antimalarial active ingredients, namely of 6-fluoro-2-(4-morpholin-4-ylmethyl-phenyl)-quinoline-4-carboxylic acid (2-pyrrolidin-1-yl-ethyl)-amide or a prodrug or salt thereof, pyronaridine or pharmaceutically acceptable salt thereof, and artemisinin or derivatives thereof. Further, pharmaceutical compositions include such combination. The combinations and pharmaceutical compositions are useful for the treatment and/or prevention of malaria.

13 Claims, No Drawings

COMBINATION OF QUINOLINE-4-CARBOXAMIDES AND BENZONAPHTHYRIDINE DERIVATIVES AS ANTIMALARIAL DRUG COMBINATION

CROSS-REFERENCE TO RELATED APPLICATIONS

This application is a National Stage entry under § 371 of International Application No. PCT/EP2019/058881 filed on Apr. 9, 2019, which claims the benefit of European Application No. 18166769.2, filed on Apr. 11, 2018. The content of each of these applications is hereby incorporated by reference in its entirety.

BACKGROUND OF THE INVENTION

Field of the Invention

The present invention relates to a combination comprising as a first active ingredient 6-fluoro-2-(4-morpholin-4-ylmethyl-phenyl)-quinoline-4-carboxylic acid (2-pyrrolidin-1-yl-ethyl)-amide or a prodrug or pharmaceutically acceptable salt thereof and as a second active ingredient pyronaridine or a prodrug or pharmaceutically acceptable salt thereof. The present invention also relates to a combination of three antimalarial active ingredients, namely of 6-fluoro-2-(4-morpholin-4-ylmethyl-phenyl)-quinoline-4-carboxylic acid (2-pyrrolidin-1-yl-ethyl)-amide or a prodrug or salt thereof, pyronaridine or pharmaceutically acceptable salt thereof, and artemisinin or derivatives thereof. The invention further relates to pharmaceutical compositions comprising such a combination and use thereof in the treatment and/or prevention of malaria.

Description of Related Art

Driven by an evolutionary phenomenon, resistance to anti-malarial medicines is a constant challenge for drug development and has led to the successive demise of first line treatments such as chloroquine, proguanil, pyrimethamine, sulphadoxine-pyrimethamine and mefloquine, which are unable to produce a 90% clinical response in many areas where they have been deployed intensively (Mita T, Tanabe K, Kita K: Spread and evolution of *Plasmodium falciparum* drug resistance. *Parasitol Int.* 2009, 58: 201-209; World Health Organization: Global report on antimalarial drug efficacy and drug resistance: 2000-2010. 2010, WHO, Geneva, 121). The artemisinin based therapy (ACTs) have since been deployed and have become the standard of care with the approval of arthemeter-lumefantrine. All ACTs are given daily over 3 days and problems with patient compliance have already been observed in every region. The rationale behind the development of artemisinin-based combination therapies was to combine a very fast-acting compound (an artemisinin derivative) that will kill >80% of the parasites within the first 24 hours (reducing symptoms rapidly) with a long acting compound, such as a 4-amino-quinoline, that will provide some protection against reinfection (post treatment prophylaxis). Currently, the emergence of resistance to artemisinin in South East Asia has been relatively slow. For the time being this translates into a decrease in parasite clearance time, as for example reported in Thailand (Phyo A P, Nkhoma S, Stepniewska K, Ashley E A, Nair S, McGready R, Ler Moo C, Al-Saai S, Dondorp A M, Lwin K M, Singhasivanon P, Day N P J, White N J, Anderson T J C, Nosten F: Emergence of artemisinin-resistant malaria on the western border of Thailand: a longitudinal study. *Lancet.* 2012, 379: 1960-1966).

As per WHO recommendation, new antimalarial should be developed as fixed dosed combination. The goal of drug combination therapy for parasitic diseases such as malaria is to prevent the emergence of resistance, while providing additional benefits for the treatment by providing a higher cure rate. The rationale being that any organism resistant to one component of the combination should be eliminated by the other, provided that both have distinct modes-of-actions. The barrier for resistance is therefore raised as the parasite would then have to acquire both resistances simultaneously, a rather unlikely scenario assuming the mutation events are stochastic (White N, Olliaro P L: Strategies for the prevention of antimalarial drug resistance: Rationale for combination chemotherapy for malaria. Parasitol Today. 1996, 12: 399-401). Noteworthy other factors that influence the emergence of drug resistance should be taken into account e.g. the effects of drug on other parasite life-cycle stages such as gametocytogenesis and gametocyte viability, drug half-life, clinical parasite reduction ratio or drug dosage (Xavier C Ding, David Ubben and Timothy N C Wells, A framework for assessing the risk of resistance for anti-malarials in development, Malaria Journal 2012, 11:292).

Over the past decade high throughput phenotypic screening campaigns has enabled the discovery of new classes of anti-malarial drugs therefore increasing the number of potential new combination therapies for the treatment of malaria and strengthening the need for a rational selection and prioritization process of the most promising ones, including and not limited to beneficial anti parasitological effect of the two chemical entities and the early assessment of the risk of developing resistance associated with each compound and each combination (Canfield C. J., Pudney M., Gutteridge W. E. Interactions of atovaquone with other antimalarial drugs against *Plasmodium falciparum* in vitro. Exp Parasitol. 1995, 80:373-81; Fivelman, Q. L., Adagu I. S., Warhurst, D. C. Modified fixed-ratio isobologram method for studying in vitro interactions between atovaquone and proguanil or dihydroartemisinin against drug-resistant strains of *Plasmodium falciparum.* Antimicrob Agents Chemother. 2004, 48:4097-4102).

BRIEF SUMMARY OF THE INVENTION

The present invention relates to a combination comprising as a first active ingredient 6-fluoro-2-(4-morpholin-4-ylmethyl-phenyl)-quinoline-4-carboxylic acid (2-pyrrolidin-1-yl-ethyl)-amide or a prodrug or pharmaceutically acceptable salt thereof and as a second active ingredient pyronaridine or a prodrug or pharmaceutically acceptable salt thereof. The present invention also relates to a combination of three antimalarial active ingredients, namely of 6-fluoro-2-(4-morpholin-4-ylmethyl-phenyl)-quinoline-4-carboxylic acid (2-pyrrolidin-1-yl-ethyl)-amide or a prodrug or salt thereof, pyronaridine or pharmaceutically acceptable salt thereof, and artemisinin or derivatives thereof. The invention further relates to pharmaceutical compositions comprising such a combination and use thereof in the treatment and/or prevention of malaria.

DETAILED DESCRIPTION OF THE INVENTION

The present invention provides a combination comprising as a first active ingredient 6-fluoro-2-(4-morpholin-4-ylmethyl-phenyl)-quinoline-4-carboxylic acid (2-pyrrolidin-1- yl-ethyl)-amide or a prodrug or pharmaceutically acceptable salt thereof and as a second active ingredient pyronaridine or a prodrug or pharmaceutically acceptable salt thereof, preferably for use in the treatment and/or prevention of malaria.

In such combinations 6-fluoro-2-(4-morpholin-4-ylmethyl-phenyl)-quinoline-4-carboxylic acid (2-pyrrolidin-1-yl-ethyl)-amide may be in the form of the free base (as shown below), but also in the form of a pharmaceutically acceptable salt (such as in particular a succinate salt):

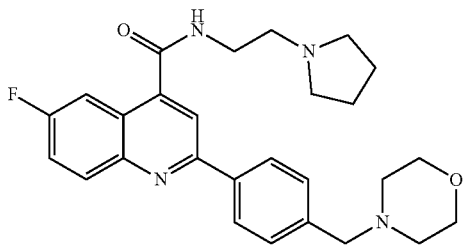

6-fluoro-2-(4-morpholin-4-ylmethyl-phenyl)-quinoline-4-carboxylic acid (2-pyrrolidin-1-yl-ethyl)-amide (free base)

Furthermore, in such combinations pyronaridine may be in the form of a free base or in the form of a pharmaceutically acceptable salt such as in particular pyronaridine tetraphosphate shown below:

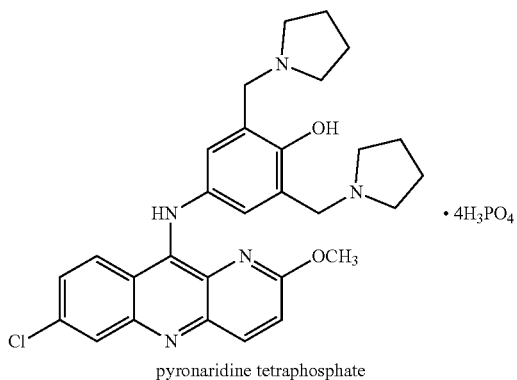

pyronaridine tetraphosphate

The above described combination according to the invention shows additive parasitological properties, and addition to this, it was surprisingly found that 6-fluoro-2-(4-morpholin-4-ylmethyl-phenyl)-quinoline-4-carboxylic acid (2-pyrrolidin-1-yl-ethyl)-amide (and any of its salts) is effluxed by P-gps and that pyronaridine, which is (unlike many other antimalarials) a P-gp inhibitor (Qi J, Yang C Z, Wang C Y, Wang S B, Yang M, Wang J H. Function and mechanism of pyronaridine: a new inhibitor of P-glycoprotein-mediated multidrug resistance. Acta Pharmacol Sin. 2002, 23:544-50), can positively affect the crossing of the gut wall of 6-fluoro-2-(4-morpholin-4-ylmethyl-phenyl)-quinoline-4-carboxylic acid (2-pyrrolidin-1-yl-ethyl)-amide (and any of its salts) wall at a lower dose, thereby positively affecting the therapeutic window.

The present invention also relates to a combination which further comprises artemisinin or a derivative or pharmaceutically acceptable salt thereof as a third active ingredient.

In a very important embodiment of such a combination according to the present invention, the artemisinin derivative is selected from a group consisting of: dihydroartemisin, artemether and artesunate.

For the purpose of this invention, the term "artesunate" is used for artesunic acid:

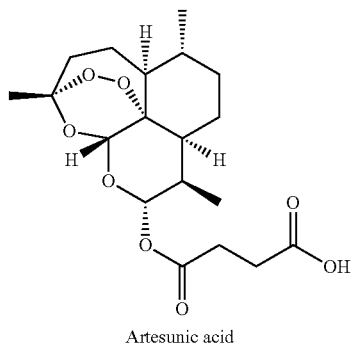 [SMILES: C[C@H]1[C@H](OC(=O)CCC(=O)O)O[C@@H]2O[C@]3(C)CC[C@H]4[C@H](C)CC[C@@H]1[C@@]24OO3]

Artesunic acid

In a specific embodiment of the present invention the third active ingredient is artesunate or a pharmaceutically acceptable salt of artesunate (preferably sodium artesunate or an alkali metal carbonate salt formed e.g. sodium carbonate or potassium carbonate).

Pharmaceutical Salts and Other Forms

The above described compounds included in the combinations can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds included in the combinations are for the most part prepared by conventional methods. If a compound included in the combinations contains an acidic center (such as e.g. artesunic acid), such as a carboxyl group, one of its suitable salts can be formed by reacting the compound with a suitable base to give the corresponding base-addition salt. Such bases are, for example, alkali metal hydroxides, including potassium hydroxide and sodium hydroxide; alkaline earth metal hydroxides, such as magnesium hydroxide and calcium hydroxide; alkali metal carbonates (such as sodium carbonate and potassium carbonate); and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine.

In the case a compound included in the combinations contains a basic center (such as e.g. 6-fluoro-2-(4-morpholin-4-ylmethyl-phenyl)-quinoline-4-carboxylic acid (2-pyrrolidin-1-yl-ethyl)amide and pyronaridine), acid-addition salts can be formed by treating these compounds with pharmaceutically acceptable organic and inorganic acids, for example hydrogen halides, such as hydrogen chloride or hydrogen bromide, other mineral acids and corresponding salts thereof.

In a specific embodiment of the present invention the pharmaceutically active salt of pyronaridine, which may be used in the combination, the pharmaceutical composition (described below) and/or the method for the treatment and/or prevention of malaria (described below), is a salt selected from a group consisting of: acetate salts, benzoate salts, besylate salts, bromide salts, camsylate salts, carbonate salts, citrate salts, chloride salts, edisylate salts, estolate salts, fumarate salts, gluceptate salts, gluconate salts, glucuronate salts, hippurate salts, iodide salts, isethionate salts, lactate salts, lactobionate salts, malate salts, maleate salts, mesylate salts, methylsulfate salts, napsylate salts, nitrate salts, oxalate salts, pamoate salts, phosphate salts (such as in particular tetraphosphate salts), stearate salts, succinate salts, sulfate salts, tartrate salts and tosylate salts; preferably the pharmaceutically active salt of pyronaridine is a salt selected from a group consisting of: acetate salts, benzoate salts, besylate salts, citrate salts, chloride salts, edisylate salts, fumarate salts, lactate salts (such as in particular L-lactate salts), malate salts (such as in particular L-malate salts), maleate salts, mesylate salts, napsylate salts, oxalate salts, phosphate salts (including in particular tetraphosphate salts), succinate salts, sulfate salts, tartrate salts (such as in particular L-tartrate salts) and tosylate salts; and even more preferably the pharmaceutically active salt of pyronaridine is a salt selected from a group consisting of: chloride salts, fumarate salts, maleate salts, mesylate salts, phosphate salts (such as in particular tetraphosphate salts), sulfate salts and tosylate salts.

In another specific embodiment of the present invention the pharmaceutically active salt of 6-fluoro-2-(4-morpholin-4-ylmethyl-phenyl)-quinoline-4-carboxylic acid (2-pyrrolidin-1-yl-ethyl)-amide, which may be used in the combination, the pharmaceutical composition (described below) and/or the method for the treatment and/or prevention of malaria (described below), is a salt selected from a group consisting of: acetate salts, benzoate salts, besylate salts, bromide salts, camsylate salts, carbonate salts, citrate salts, chloride salts, edisylate salts, estolate salts, fumarate salts, gluceptate salts, gluconate salts, glucuronate salts, hippurate salts, iodide salts, isethionate salts, lactate salts, lactobionate salts, malate salts, maleate salts, mesylate salts, methylsulfate salts, napsylate salts, nitrate salts, oxalate salts, pamoate salts, phosphate salts (such as in particular tetraphosphate salts), stearate salts, succinate salts, sulfate salts, tartrate salts and tosylate salts; preferably the pharmaceutically active salt of pyronaridine is a salt selected from a group consisting of: acetate salts, benzoate salts, besylate salts, citrate salts, chloride salts, edisylate salts, fumarate salts, lactate salts (such as in particular L-lactate salts), malate salts (such as in particular L-malate salts), maleate salts, mesylate salts, napsylate salts, oxalate salts, phosphate salts, succinate salts, sulfate salts, tartrate salts (such as in particular L-tartrate salts) and tosylate salts; and even more preferably the pharmaceutically active salt of pyronaridine is a salt selected from a group consisting of: chloride salts, fumarate salts, maleate salts, mesylate salts, phosphate, sulfate salts and tosylate salts.

In another specific embodiment of the present invention the pharmaceutically active salt of artesunate, which may be used in the combination, the pharmaceutical composition (described below) and/or the method for the treatment and/or prevention of malaria (described below), is a salt selected from a group consisting of: sodium salts and potassium salts.

A particular embodiment of the present invention relates to a combination, which comprises (a) 6-fluoro-2-(4-morpholin-4-ylmethyl-phenyl)-quinoline-4-carboxylic acid (2-pyrrolidin-1-yl-ethyl)-amide (free base) or 6-fluoro-2-(4-morpholin-4-ylmethyl-phenyl)-quinoline-4-carboxylic acid (2-pyrrolidin-1-yl-ethyl)-amide succinate and (b) pyronaridine tetraphosphate or pyronaridine (free base). In even more specific embodiment the combination comprises (a) 6-fluoro-2-(4-morpholin-4-ylmethyl-phenyl)-quinoline-4-carboxylic acid (2-pyrrolidin-1-yl-ethyl)-amide (free base) or 6-fluoro-2-(4-morpholin-4-ylmethyl-phenyl)-quinoline-4-carboxylic acid (2-pyrrolidin-1-yl-ethyl)amide succinate and (b) pyronaridine tetraphosphate.

In another embodiment the combination comprises a) 6-fluoro-2-(4-morpholin-4-ylmethyl-phenyl)-quinoline-4-carboxylic acid (2-pyrrolidin-1-yl-ethyl)amide (free base) or 6-fluoro-2-(4-morpholin-4-ylmethyl-phenyl)-quinoline-4-carboxylic acid (2-pyrrolidin-1-yl-ethyl)amide succinate, b) pyronaridine (free base) or pyronaridine tetraphosphate and c) artesunate or sodium artesunate.

In very specific embodiment the combination comprises a) 6-fluoro-2-(4-morpholin-4-ylmethyl-phenyl)-quinoline-4-carboxylic acid (2-pyrrolidin-1-yl-ethyl)-amide (free base) or 6-fluoro-2-(4-morpholin-4-ylmethyl-phenyl)-quinoline-4-carboxylic acid (2-pyrrolidin-1-yl-ethyl)amide succinate, b) pyronaridine tetraphosphate and c) sodium artesunate.

The active ingredients of the combinations according to the invention are administered simultaneously or sequentially (spread out over time).

In case the administration of the active ingredients is carried out simultaneously, the two or three active ingredients may be combined within a single pharmaceutical form (fixed combination, such as e.g. a tablet or a sachet). Independently of whether the administration of the active ingredients is simultaneous or non-simultaneous or, in case of three active ingredients, partly simultaneous, the two or three active ingredients may be present in distinct pharmaceutical forms. In this case the combinations according to the invention may be in the form of a kit.

Another aspect of the present invention relates to the herein discloses combination as medicaments. Furthermore, the present invention relates to the use of the combinations described herein in the treatment and/or prevention of malaria. The present invention also encompasses the use of a combination described herein for the manufacture of a medicament for the treatment and/or prevention of malaria.

Pharmaceutical Compositions

The present invention also relates to a pharmaceutical composition, preferably for use in the treatment and/or prevention of malaria, comprising as a first active ingredient 6-fluoro-2-(4-morpholin-4-ylmethyl-phenyl)-quinoline-4-carboxylic acid (2-pyrrolidin-1-yl-ethyl)-amide or a prodrug or pharmaceutically acceptable salt thereof and as a second active ingredient pyronaridine or a pharmaceutically acceptable salt thereof as active ingredients, both active ingredients preferably in therapeutically active doses.

The present invention further relates to a pharmaceutical composition, preferably for use in the treatment and/or prevention of malaria, comprising as a first active ingredient 6-fluoro-2-(4-morpholin-4-ylmethyl-phenyl)-quinoline-4-carboxylic acid (2-pyrrolidin-1-yl-ethyl)-amide or a prodrug or pharmaceutically acceptable salt thereof, as a second active ingredient pyronaridine or a pharmaceutically acceptable salt thereof as active ingredients, and as a third active ingredient artemisinin or a derivative thereof. Preferably, such a composition comprises all three active ingredients in a therapeutically effective amount. In a preferred embodiment the third active ingredient is artesunate or a pharmaceutically acceptable salt thereof such as e.g. sodium artesunate).

The present invention also relates to a pharmaceutical composition comprising as active ingredients therapeutically active doses of 6-fluoro-2-(4-morpholin-4-ylmethyl-phenyl)-quinoline-4-carboxylic acid (2-pyrrolidin-1-yl-ethyl)amide or a prodrug or pharmaceutically acceptable salt thereof and pyronaridine or a pharmaceutically acceptable salt thereof, and also at least one pharmaceutically acceptable excipient, for the treatment and/or prevention of malaria. A specific embodiment of such a pharmaceutical composition comprises as a further active ingredient a therapeutically active dose of artemisinin or a derivative or pharmaceutically acceptable salt thereof.

Pharmaceutical compositions can be administered in the form of dosage units, which comprise a predetermined amount of active ingredient per dosage unit. Such a unit can comprise different doses of a combination according to the invention, depending on the disease condition treated, the method of administration and the age, weight and condition of the patient, or pharmaceutical compositions can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical compositions of this type can be prepared using a process, which is generally known in the pharmaceutical art.

Pharmaceutical compositions can be adapted for administration via any desired suitable method, for example by oral (including buccal or sublingual), rectal, nasal, topical (including buccal, sublingual or transdermal) or parenteral (including subcutaneous, intramuscular, intravenous or intradermal) methods. Such compositions can be prepared using all processes known in the pharmaceutical art by, for example, combining the active ingredient with the excipient(s) or adjuvant(s).

Pharmaceutical compositions adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions. Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubilizer, such as, for example, agar-agar, calcium carbonate or sodium carbonate, may likewise be added in order to improve the availability of the medicament after the capsule has been taken. In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like.

The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinyl-pyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mutated by dispersion of the compounds in a non-toxic vehicle. Solubilizers and emulsifiers, such as, for example, ethoxylated isostearyl alcohols and polyoxy ethylene sorbitol ethers, preservatives, flavour additives, such as, for example, peppermint oil or natural sweeteners or saccharin, or other artificial sweeteners and the like, can likewise be added. The dosage unit formulations for oral administration can, if desired, be encapsulated in microcapsules. The formulation can also be prepared in such a way that the release is extended or retarded, such as, for example, by coating or embedding of particulate material in polymers, wax and the like.

The active ingredients of the combinations according to the present invention and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

Pharmaceutical compositions adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986). Pharmaceutical compounds adapted for topical administration can be formulated as ointments, creams, suspensions, lotions, powders, solutions, pastes, gels, sprays, aerosols or oils. Pharmaceutical compositions adapted for rectal administration can be administered in the form of suppositories or enemas. Injection solutions and suspensions prepared in accordance with the recipe can be prepared from sterile powders, granules and tablets.

It goes without saying that, in addition to the above particularly mentioned constituents, the compositions may also comprise other agents usual in the art with respect to the particular type of formulation; thus, for example, compositions which are suitable for oral administration may comprise flavours.

The pharmaceutical compositions/formulations according to the invention can be used as medicaments in human and veterinary medicine.

A therapeutically effective amount or therapeutically active dose of each of the active ingredients of the combination according to the invention and of the other active ingredient depends on a number of factors, including, for example, the age and weight of the animal, the precise disease condition which requires treatment, and its severity, the nature of the formulation and the method of administration, and is ultimately determined by the treating doctor or vet.

For oral administration of a combination according the present invention containing 6-fluoro-2-(4-morpholin-4-ylmethyl-phenyl)-quinoline-4-carboxylic acid (2-pyrrolidin-1-yl-ethyl)-amide succinate salt and pyronaridine tetraphosphate salt as active ingredients, the daily doses of these two active ingredients are as follows:

6-fluoro-2-(4-morpholin-4-ylmethyl-phenyl)-quinoline-4-carboxylic acid (2-pyrrolidin-1-yl-ethyl)-amide succinate salt: between 30 mg and 1000 mg, preferably between 100 mg and 700 mg even more preferably between 300 mg and 600 mg per individual per day (single dose).

Pyronaridine tetraphosphate salt: between 180 mg and 1000 mg, preferably between 300 and 800 mg even more preferably between 400 mg and 600 mg per individual per day (single dose).

For oral administration of a combination according the present invention containing 6-fluoro-2-(4-morpholin-4-ylmethyl-phenyl)-quinoline-4-carboxylic acid (2-pyrrolidin-1-yl-ethyl)-amide succinate salt, pyronaridine tetraphosphate salt and artesunate as active ingredients, the daily doses of each of these three active ingredients are as follows:

6-fluoro-2-(4-morpholin-4-ylmethyl-phenyl)-quinoline-4-carboxylic acid (2-pyrrolidin-1-yl-ethyl)-amide succinate salt: between 30 mg and 1000 mg, preferably between 100 mg and 700 mg even more preferably between 300 mg and 600 mg per individual per day (single dose).

Pyronaridine tetraphosphate salt: between 180 and 1000 mg, preferably between 300 and 800 mg even more preferably between 400 mg and 600 mg per individual per day (single dose).

Artesunate: between 20 and 200 mg, preferably between 100 and 200 mg even more preferably between 150 mg and 180 mg per individual per day (single dose).

The combinations/pharmaceutical compositions according to the present invention can be used as medicaments in human and veterinary medicine.

In another aspect, the present invention relates to a method for the treatment and/or prevention of malaria in a patient in need thereof, comprising administering to such patient a therapeutically active amount of a combination of 6-fluoro-2-(4-morpholin-4-ylmethyl-phenyl)-quinoline-4-carboxylic acid (2-pyrrolidin-1-yl-ethyl)-amide (first active ingredient) and pyronaridine (second active ingredient) or a prodrug or pharmaceutically acceptable salt of any of the any of the foregoing including mixtures thereof in all ratios. In a specific embodiment of such a method according to the invention also artemisinin or a derivative or pharmaceutically acceptable salt thereof is administered to the patient (as a third active ingredient).

In a further aspect, the present invention relates to a kit (consisting of separate packs) for the treatment of malaria, comprising firstly 6-fluoro-2-(4-morpholin-4-ylmethyl-phenyl)-quinoline-4-carboxylic acid (2-pyrrolidin-1-yl-ethyl) amide or a pharmaceutically active salt thereof, and secondly pyronaridine or a pharmaceutically active salt thereof.

Another embodiment relates to a kit as described above, wherein the kit further comprises thirdly artemisinin or a derivative or pharmaceutically acceptable salt thereof (preferably the kit further comprises artesunate (preferably sodium artesunate) of artesunic acid).

For the propose of the present invention, the expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

As used herein and unless otherwise indicated, the term "prodrug" means a derivative of an active ingredient that can hydrolyze, oxidize, or otherwise react under biological conditions (in vitro or in vivo) to provide an active compound. Examples of prodrugs include, but are not limited to, derivatives and metabolites of an active ingredient that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

EXAMPLES

Unless otherwise specified, all starting materials are obtained from commercial suppliers and used without further purifications. Unless otherwise specified, all temperatures are expressed in ° C. and all experiments are conducted at RT.

ABBREVIATIONS

ACT artemisinin based therapy
Ci curie
Cpm counts per minute
CsA cyclosporine A
DMEM Dulbecco's Modified Eagle Medium
DMSO dimethyl sulfoxide
HBSS Hank's Buffered Salt Solution HEPES 4-(2-hydroxyethyl)piperazine-1-ethanesulfonic acid
HESI Heated Electrospray Ionization
LC liquid chromatography
M1 6-fluoro-2-(4-morpholin-4-ylmethyl-phenyl)-quinoline-4-carboxylic acid (2-pyrrolidin-1-yl-ethyl)amide succinate salt
MS mass spectrometry
*P. falciparum* Plasmodium falciparum
P-gp P-glycoprotein
po Per os (oral)
PYRO pyronaridine tetraphosphate salt
RT room temperature
RPMI Roswell Park Memorial Institute medium
SCID Severe Combined Immuno Deficiency The invention will be illustrated (but not limited), by reference to the specific embodiments described in the following examples.

I. In Vitro Isobolograms

Compounds are tested against intraerythrocytic forms of *P. falciparum* derived from asynchronous stock cultures of lab strain NF54 (Schiphol airport strain of unknown origin), as described in Desjardins, R. E., Canfield, C. J., Haynes, J. D. & Chulay, J. D. Quantitative assessment of antimalarial activity in vitro by a semiautomatic microdilution technique. Antimicrob. Agents Chemother. 1979, 16: 710-718 and Matile, H. and Pink, J. R. L. *Plasmodium falciparum* malaria parasite cultures and their use in immunology. Immunological Methods IV, 221-234 Academia Press (1990) using a mixture consisting of RPMI 1640 supplemented with 0.5% ALBUMAX® II, 25 mM HEPES, 25 mM $NaHCO_3$ (pH 7.3), 0.36 mM hypoxanthine and 100 µg/ml neomycin as a culture medium. Human type A+ erythrocytes serve as host cells. The cultures are kept at 37° C. in an atmosphere of 3% $O_2$, 4% $CO_2$ and 93% $N_2$ in humidified modular chambers. Testing of the individual drugs is carried out in 96-well microtiter plates. The compounds are dissolved in DMSO (10 mg/ml), prediluted in hypoxanthine-free culture medium and titrated in 100 µl duplicates over a 64-fold range. After addition of an equal volume of parasite culture with a parasitemia of 0.3% in a 2.5% erythrocyte suspension, the test plates are incubated under the conditions described above for 24 h, 48 h or 72 h. Parasite growth is measured by the incorporation of radiolabelled [$^3$H]hypoxanthine (0.25 µCi in a volume of 50 µl hypoxanthine-free culture medium) added 8 h (for 24 h assay duration) or 24 h (48 h and 72 h assay duration) prior to the termination of the test. Cultures are harvested onto glass-fiber filters and washed with distilled water. The radioactivity is counted using a MicroBetaplate liquid scintillation counter (Wallac, Zürich, Switzerland) and the results are recorded as counts per minute per well at each drug concentration and expressed as percentage of the untreated controls. Fifty percent inhibitory concentrations ($IC_{50}$) are determined by linear interpolation (Huber, W., Hurt, N., Mshinda, H., Jaquet, C., Koella, J. C., Tanner, M. Sensitivity of *Plasmodium falciparum* field-isolates from Tanzania to chloroquine, mefloquine and pyrimethamine during in vitro cultivation. Acta Trop. 1993, 52: 313-6).

Drug interaction studies are performed as described in Canfield C. J., Pudney M., Gutteridge W. E. Interactions of atovaquone with other antimalarial drugs against *Plasmodium falciparum* in vitro. Exp Parasitol. 1995, 80:373-81 and Fivelman, Q. L., Adagu I. S., Warhurst, D. C. Modified Fixed-ratio isobologram method for studying in vitro interactions between atovaquone and proguanil or dihydroartemisinin against drug-resistant strains of *Plasmodium falciparum*. Antimicrob Agents Chemother. 2004, 48: 4097-4102. Initially, the $IC_{50}$ of the test drugs alone is determined (see above). Subsequently, drug solutions are diluted with hypoxanthine-free culture medium to initial concentrations of 10 times the predetermined $IC_{50}$. The solutions (all at $10 \times IC_{50}$) are combined in ratios of 1+3, 1+1 or 3+1. Single and combination drug solutions are then introduced into 96-well plates to give duplicate rows. The rest of the procedure is as described above. For data interpretation, the $IC_{50}$s of the drugs in combination are expressed as fractions of the $IC_{50}$s of the drugs alone. These fractions are called "Fractional Inhibitory Concentrations" (FIC) for drug A and for drug B, respectively.

$$FIC\ Drug\ A = \frac{IC50\ A(B)}{IC50\ A}$$

FIC Drug A: Fractional inhibitory concentration
$IC_{50}$ A (B): 50% inhibitory concentration of drug A in presence of drug B
$IC_{50}$ A: 50% inhibitory concentration of drug A alone Numeric values for the interaction are obtained and expressed as the sum of the FICA and FICB. Sum FIC values indicate the kinds of interaction as follows:

Antagonism when ΣFIC>4.0, no detrimental interaction when ΣFIC>0.5-4.0 (Odds, F. C., Antimicrob Agents Chemother. 2003, 52: 1).

TABLE 1

In vitro drug combination assays for M1 + PYRO.

| Combination ratio | Drugs Partners | ΣFIC NF54 24 h | ΣFIC NF54 48 h | ΣFIC NF54 72 h | Interaction 72 h |
|---|---|---|---|---|---|
| 1 + 3 | M1 + PYRO | 1.4 | 1.7 | 1.4 ± 0.12 | No detrimental interaction |
| 1 + 1 | M1 + PYRO | 1.6 | 1.5 | 1.4 ± 0.26 | No detrimental interaction |
| 3 + 1 | M1 + PYRO | 1.3 | 1.3 | 1.4 ± 017 | No detrimental interaction |

ΣFIC (Fractional Inhibitory Concentrations), antagonism when ΣFIC > 4.0, no detrimental interaction when ΣFIC > 0.5-4.0 The values show the mean of ≥3 independent assays for K1 and NF54, respectively.
M1 was combined individually with PYRO. For the NF54 *P. falciparum* strain with the three different assay durations (24 h, 48 h and standard 72 h), the $ΣFIC_{50}$ values were calculated from ≥3 independent experiments. They were in the range of 1.3-1.7, suggesting that the interaction between M1 and PYRO under the given test conditions is a non-detrimental (Table 1).

II. In Vivo SCID Mouse Model

Compound efficacy was assessed against the *Plasmodium falciparum* strain Pf3D7$^{0087/N9}$ in vivo. Mice are infected intravenously with parasitized red blood cells on day 0. Experimental mice are generally treated at day 3, 4, 5, and 6 post-infection with an oral dose of the compound (single or 4-day oral dosing regimen) and are compared to an infected control group for reduction in parasitemia on day 7 (Maria Belen Jimenez-Díaz, Teresa Mulet, Sara Viera, Vanessa Gomez, Helen Garuti, Javier Ibanez, Angela Alvarez-Doval, Leonard D. Shultz, Antonio Martínez, Domingo Gargallo-Viola, and Inigo Angulo-Barturen, Improved Murine Model of Malaria Using *Plasmodium falciparum* Competent Strains and Non-Myelodepleted NOD-scid IL2Rgammanull Mice Engrafted with Human Erythrocytes, Antimicrob Agents Chemother. 2009, 53:4533).

Vehicle

PYRO and M1 were solubilized in a vehicle consisting of 70% Tween-80 and 30% ethanol, followed by a 10-fold dilution in $H_2O$. All preparations resulted in a yellow, liquid and clear solution.

Pharmacokinetic Analysis

The blood levels of the test compound are evaluated in order to determine standard pharmacokinetic parameters in the individuals of the efficacy study. Peripheral blood samples (20 µl) are taken at different times (see protocol below), mixed with 20 µl of $H_2O$ Milli Q and immediately frozen on dry ice. The frozen samples are stored at −80° C. until analysis. Blood from control mice is used for calibration and QC purposes. Blood samples are processed under standard liquid-liquid extraction conditions and analyzed by LC-MS/MS (quantification by HESI ionization in positive ion mode).

TABLE 2

Oral therapeutic efficacy of pyronaridine against *P. falciparum* Pf3D7[0087/N9] during a 4-day dosing in SCID mice.

| DAYS POST INFECTION | % PARASITEMIA[2] | | | | | % control | Activity | N[3] |
|---|---|---|---|---|---|---|---|---|
| | 3 | 4 | 5 | 6 | 7 | | | |
| CONTROL[1] | 0.7 | 1.26 | 3.31 | 5.35 | 9.14 | — | — | 4 |
| PYRO (4 × 1 MG/KG) | 0.63 | 1.21 | 3.14 | 4.53 | 7.55 | 82.6 | 17.4% | 2 |
| PYRO (4 × 3 MG/KG) | 0.71 | 1 | 0.44 | 0.25 | 0.04 | 0.4 | 99.6% | 2 |
| PYRO (4 × 9 MG/KG) | 0.7 | 0.28 | 0.15 | 0.063 | <LLQ | <LLQ | 100% | 2 |

[1]no treatment;

[2]mean value;

[3]number of mice per group;

LLQ = Lower Limit of Quantification (<0.01% parasitemia).

From table 2, at day 7 post-infection, 9 mg/kg po of pyronaridine showed >99.9% activity and parasite-free at day 7. The 3 mg/kg showed 99.6% activity and the remaining doses of 1 mg/kg showed minute activity (17%) compared to untreated control mice. PYRO induced clearance of parasites from peripheral blood comparable to 50 mg/kg of chloroquine in the very same experimental system. The $ED_{90}$ (i.e. the dose of PYRO in mg/kg that reduces parasitemia at day 7 post-infection by 90% with respect to untreated control mice) could not be accurately determined due to the limited number of doses but could be narrowed down to a range between 1 and 3 mg/kg.

TABLE 3

Oral therapeutic efficacy of M1 against *P. falciparum* pf3D7[0087/N9] during a 4-day dosing in SCID mice.

| DAYS POST INFECTION | % PARASITEMIA[2] | | | | | % control | Activity | N[3] |
|---|---|---|---|---|---|---|---|---|
| | 3 | 4 | 5 | 6 | 7 | | | |
| CONTROL[1] | 0.70 | 1.26 | 3.31 | 5.35 | 9.14 | — | — | 4 |
| M1 (4 × 0.2 MG/KG) | 0.85 | 1.33 | 3.10 | 3.35 | 6.55 | 71.7 | 28.3% | |
| M1 (4 × 0.4 MG/KG) | 0.70 | 1.38 | 1.18 | 0.75 | 0.55 | 6.0 | 94.0% | 2 |
| M1 (4 × 0.6 MG/KG) | 0.63 | 0.70 | 0.60 | 0.13 | 0.03 | 0.3 | 99.7% | 2 |
| M1 (4 × 1.2 MG/KG) | 0.50 | 0.75 | 0.43 | 0.05 | <LLQ | <LLQ | 100% | 2 |

[1]no treatment;

[2]mean value;

[3]number of mice per group;

LLQ = Lower Limit of Quantification (<0.01% parasitemia).

From Table 3, at day 7 post-infection, 1.2 mg/kg po of M1 showed >99.9% activity. The 0.6 and 0.4 mg/kg showed 99.7% and 94.9% activity respectively and the remaining doses of 0.2 mg/kg showed minute activity (28.3%), compared to untreated control mice.

M1 induced clearance of parasites comparable (but slower) to 50 mg/kg of chloroquine in the same experimental system. The $ED_{90}$ was calculated to be 0.37 mg/kg (free base) (María Belen Jimenez-Díaz, Teresa Mulet, Sara Viera, Vanessa Gomez, Helen Garuti, Javier Ibanez, Angela Alvarez-Doval, Leonard D. Shultz, Antonio Martínez, Domingo Gargallo-Viola, and Inigo Angulo-Barturen, Improved Murine Model of Malaria Using *Plasmodium falciparum* Competent Strains and Non-Myelodepleted NOD-scid IL2Rgammanull Mice Engrafted with Human Erythrocytes, Antimicrob Agents Chemother. 2009, 53:4533).

TABLE 4

Oral therapeutic efficacy of M1 + PYRO combination against *P. falciparum* pf3D7[0087/N9] during a 4-day dosing.

| ENTRY | | | days post infection | % PARASITEMIA[2] | | | | | | N[3] |
|---|---|---|---|---|---|---|---|---|---|---|
| | | | | 3 | 4 | 5 | 6 | 7 | 10 | |
| 1 | M1 (0 mg/kg) | PYRO (0 mg/kg) | | 1.07 | 2.18 | 5.04 | 9.15 | 12 | X | 4 |
| 2 | M1 (4 × 1.2 mg/kg) | PYRO (0 mg/kg) | | 0.99 | 1.04 | 0.7 | 0.12 | 0.01 | <LLQ | 2 |
| 3 | M1 (0 mg/kg) | PYRO (4 × 3 mg/kg) | | 1.16 | 0.67 | 0.08 | 0.01 | <LLQ | <LLQ | 2 |
| 4 | M1 (4 × 0.4 mg/kg) | PYRO (4 × 3 mg/kg) | | 0.96 | 0.70 | 0.09 | <LLQ | <LLQ | <LLQ | 2 |
| | | ratio | | 1.21 | 0.94 | 0.88 | ND | ND | ND | — |
| 5 | M1 (0 mg/kg) | PYRO (4 × 9 mg/kg) | | 1.09 | 0.34 | 0.05 | <LLQ | <LLQ | <LLQ | 2 |
| 6 | M1 (4 × 1.2 mg/kg) | PYRO (4 × 9 mg/kg) | | 1.18 | 0.14 | 0.06 | 0.01 | <LLQ | <LLQ | 2 |
| | | ratio | | 0.93 | 2.41 | 0.83 | ND | ND | ND | — |
| 7 | M1 (0 mg/kg) | PYRO (4 × 30 mg/kg) | | 1.13 | 0.14 | 0.02 | 0.01 | <LLQ | <LLQ | 2 |
| 8 | M1 (4 × 1.2 mg/kg) | PYRO (4 × 30 mg/kg) | | 1.07 | 0.17 | 0.03 | 0.01 | <LLQ | <LLQ | 2 |
| | | ratio | | 1.06 | 0.83 | 0.50 | 1.00 | ND | ND | — |

[1]control;
[2]mean value;
[3]number of mice per group;
LLQ = Lower Limit of Quantification (<0.01% parasitemia); ND = Not determined.

Table 4 summarizes the pharmacodynamic data (% parasitemia) when M1 and pyronaridine are combined in the same experimental in vivo system.

Entry 1 displays the % parasitemia when the group in untreated (control) allowing the parasitemia to reach 12% of total erythrocytes at day 7 post infection. Entry 2 displays the % parasitemia of M1 at the maximum parasitological concentration (MPC) and a lag phase of 48 h could be observed before parasite clearance is effective to reach the LLQ at day 10.

Based on the ratio of % parasitemia in the combination arm versus alone as indicated in PYRO entries 3&4, 5&6 and 7&8, it appears that M1 does not impact the clearance of parasites induced by PYRO at day 4&5 when fast killing of parasites is required.

III. In Vitro Permeability in Caco-2 Cells

Caco-2 cells are maintained in DMEM in an atmosphere of 8.5% $CO_2$. For transport experiments $0.125 \times 10^6$ cells/well of are seeded on polycarbonate filter inserts and are allowed to grow and differentiate for 14±1 days before the cell monolayers are used for experiments. Drug transport experiments are carried out using a cocktail approach in a four-dimensional setting. Apparent permeability coefficients are determined for A (apical)→B (basolateral) and B→A directions with and without the presence of CsA as a transporter inhibitor. Up to five test items and reference compounds are dissolved in Hank's balanced salt solution at pH 7.4 to yield a final concentration of 1 μM. The assays are performed in HBSS containing 25 mM HEPES (pH 7.4) in an atmosphere of 5% $CO_2$ at 37° C. Prior to the study, the monolayers are washed in pre-warmed HBSS. At the start of the experiments pre-warmed HBSS containing the test items is added to the donor side of the monolayer and HBSS without test items is added to the receiver side. The plates are shaken at 150 rpm at 37° C. during the experiment. After 2 h the Transwell insert containing the monolayer is carefully removed and placed in a new plate and aliquots of both the receiver and donor sides were taken and diluted with an equal volume of acetonitrile containing the internal standard. The mixture is centrifuged and supernatant analyzed by LC-MS/MS. The apparent permeability coefficients (Papp) are calculated using the formula:

$$Papp=[Vrec/(A \times C0, donor)](dCrec/dt) \times 10^6$$

with dCrev/dt being the change in concentration in the receiver compartment with time, Vrec the volume of the sample in the receiver compartment, C0, donor the concentration in the donor compartment at time 0, and A the area of the compartment with the cells.

TABLE 7

Permeability coefficient and ratio for M1 in Caco-2 monolayer
in the presence or absence of Cyclosporine A.

| DIRECTION[1] | P-GP INHIBITOR | PAPP (10E−6 CM/S) | RECOVERY (%) | EFFLUX RATIO |
|---|---|---|---|---|
| APICAL TO BASOLATERAL (A-B) | no | 2.97 | 79.8 | 18.2 |
| BASOLATERAL TO APICAL (B-A) | no | 54.2 | 65.4 | |
| APICAL TO BASOLATERAL (A-B) | CsA[2] | 14.4 | 72.5 | 1.53 |
| BASOLATERAL TO APICAL (B-A) | CsA[2] | 22 | 86.3 | |

[1]pH in Apical/Basolateral chambers was 7.4/7.4.
[2]Cyclosporine A ncubated at 10 μM.

In Caco-2 monolayer cells, M1 is effluxed by P-gp transporters with a ratio of 18.2 (Table 7). The permeability can be restored by means of a P-gp inhibitor like CsA as the ratio drop to 1.53 to allow a similar rates for M1 to cross from the apical to basolateral and basolateral to apical side of the Caco-2 monolayer.

TABLE 8

Permeability coefficient and ratio for M1 in Caco-2
monolayer in the presence or absence of PYRO.

| CONCENTRATION OF PYRO (μM) | PAPP (10E−6 CM/S) | PAPP (A-B)[2] (10E−6 CM/S) | PAPP (B-A)[3] (10E−6 CM/S) | EFFLUX RATIO |
|---|---|---|---|---|
| 0 | 7.8 | 2.00 | 30.55 | 15.44 |
| 0.3 | 9.74 | 3.07 | 30.90 | 10.07 |
| 1 | 8.25 | 2.17 | 31.40 | 14.47 |
| 3 | 12.27 | 3.85 | 39.10 | 10.16 |
| 10 | 11.34 | 3.42 | 37.60 | 10.99 |
| 30 | 16.40 | 7.29 | 36.90 | 5.06 |
| 100 | 30.02 | 19.30 | 46.70 | 2.42 |

[1]pH in Apical/Basolateral chambers was 7.4/7.4.
[2]APICAL TO BASOLATERAL.
[3]BASOLATERAL TO APICAL Permeability of M1 increased with increasing concentrations of PYRO with PappA-B=2.00 without PYRO to 19.3 at 100 μM PYRO. Efflux ratios decreased from 15.44 without PYRO to 2.42 with 100 μM of Pyronaridine.

PYRO inhibited Pgp-mediated efflux of M1 at concentrations greater than 10 μM.

The invention claimed is:

1. A combination, comprising:
    as a first active ingredient, 6-fluoro-2-(4-morpholin-4-ylmethyl-phenyl)-quinolino-4-carboxylic acid (2-pyrrolidin-1-yl-ethyl)-amide or a pharmaceutically acceptable salt thereof, and
    as a second active ingredient, pyronaridine or a pharmaceutically acceptable salt thereof.

2. The combination according to claim 1, which further comprises:
    as a third active ingredient, artemisinin or a derivative or pharmaceutically acceptable salt thereof.

3. The combination according to claim 2, wherein the artemisinin derivative is selected from the group consisting of dihydroartemisin, artemether, and artesunate.

4. The combination according to claim 3, wherein the third active ingredient is artesunate or a pharmaceutically acceptable salt thereof.

5. The combination according to claim 4, wherein the pharmaceutically acceptable salt of artesunate is salt selected from the group consisting of sodium salts and potassium salts.

6. The combination according to claim 2, wherein the combination comprises:
    6-fluoro-2-(4-morpholin-4-ylmethyl-phenyl)-quinoline-4-carboxylic acid (2-pyrrolidin-1-yl-ethyl)-amide,
    pyronaridine tetraphosphate, and
    sodium artesunate.

7. The combination according to claim 1, wherein the first active ingredient and the second active ingredient are administered simultaneously or sequentially.

8. A pharmaceutical composition, comprising:
    as active ingredients,
        therapeutically active doses of 6-fluoro-2-(4-morpholin-4-ylmethyl-phenyl)-quinoline-4-carboxylic acid (2-pyrrolidin-1-yl-ethyl)-amide or a pharmaceutically acceptable salt thereof, and
        pyronaridine or a pharmaceutically acceptable salt thereof, and
    at least one pharmaceutically acceptable excipient,
    for the treatment and/or prevention of malaria.

9. The pharmaceutical composition according to claim 8, comprising:
    as a further active ingredient, a therapeutically active dose of artemisinin or a derivative or pharmaceutically acceptable salt thereof.

10. A kit for the treatment of malaria, comprising:
    firstly 6-fluoro-2-(4-morpholin-4-ylmethyl-phenyl)-quinoline-4-carboxylic acid (2-pyrrolidin-1-yl-ethyl)-amide or a pharmaceutically active salt thereof, and
    secondly pyronaridine or a pharmaceutically active salt thereof.

11. The kit according to claim 10, which further comprises:
    artemisinin or a derivative or pharmaceutically acceptable salt thereof.

12. A method for the treatment and/or prevention of malaria in a patient in need thereof, comprising:
    administering to such patient a therapeutically active amount of a combination of 6-fluoro-2-(4-morpholin-4-ylmethyl-phenyl)-quinoline-4-carboxylic acid (2-pyrrolidin-1-yl-ethyl)-amide or a pharmaceutically acceptable salt thereof, and
    pyronaridine or a pharmaceutically acceptable salt thereof, including mixtures thereof in all ratios.

13. The method according to claim 12, wherein the combination further comprises artemisinin or a derivative or pharmaceutically acceptable salt thereof.

* * * * *